United States Patent [19]

Fridy

[11] 4,160,314
[45] Jul. 10, 1979

[54] DEGRAINING, A THREE STEP PROCESS TO OBTAIN PROPELLANT SAMPLES FROM CASE BONDED MOTORS

[75] Inventor: Levi G. Fridy, Hillcrest Heights, Md.

[73] Assignee: The United States of America as represented by the Secretary of the Navy, Washington, D.C.

[21] Appl. No.: 901,163

[22] Filed: Apr. 28, 1978

[51] Int. Cl.² .................... B23P 1/00; B23P 13/04
[52] U.S. Cl. .................................. 29/558; 29/56.5; 83/651.1; 204/129.6; 204/224 M
[58] Field of Search .................. 204/224 M, 129.6; 83/171, 200.1, 651.1; 408/1; 29/56.5, 558

[56] References Cited

U.S. PATENT DOCUMENTS

| 1,906,582 | 5/1933 | Gundlach | 83/200.1 X |
| 2,489,784 | 11/1949 | Kerr | 83/200.1 |
| 2,506,377 | 5/1950 | Miller | 83/651.1 X |
| 2,741,594 | 4/1956 | Bowersett | 204/224 M X |
| 3,365,381 | 1/1968 | Fromson | 204/224 M X |
| 3,456,541 | 7/1969 | Thompson et al. | 83/415 |
| 3,503,122 | 3/1970 | Albrektson | 408/1 X |
| 3,775,127 | 8/1973 | Tyler et al. | 204/224 M |

FOREIGN PATENT DOCUMENTS

| 1005458 | 9/1963 | United Kingdom | 204/224 M |
| 192581 | 2/1967 | U.S.S.R. | 204/224 M |

Primary Examiner—Z. R. Bilinsky
Attorney, Agent, or Firm—R. S. Sciascia; A. L. Branning; H. B. Field

[57] ABSTRACT

A process for obtaining propellant samples from case bonded motors comprises the use of electrolytic machining to remove two narrow bands of the case to expose the propellant liner, severing of the sample section from the rocket motor by means of a piano wire cutter, and removal of the propellant sample by means of a spool type piano wire cutter.

3 Claims, 6 Drawing Figures

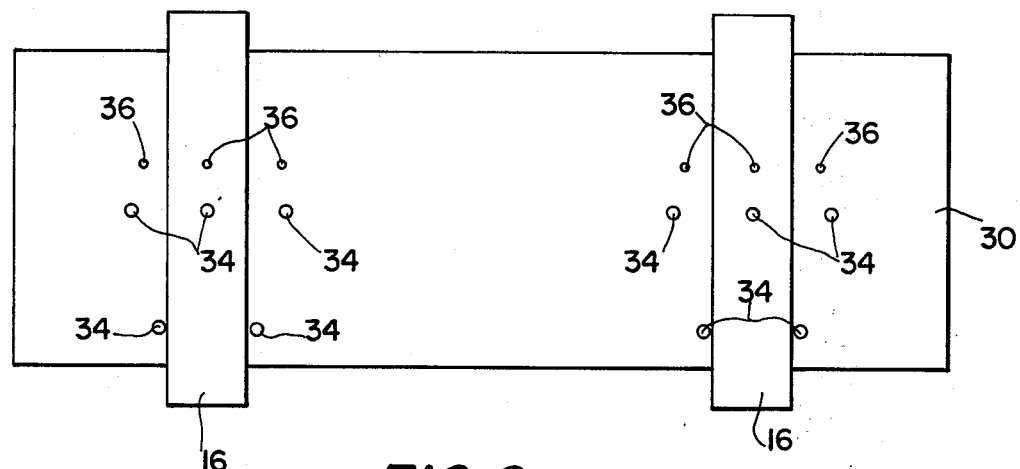
FIG. 2
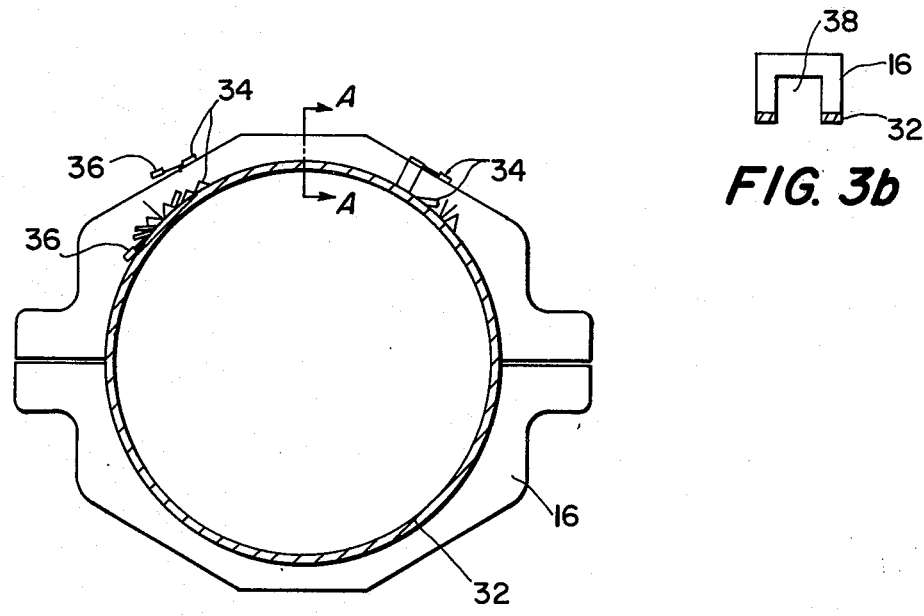
FIG. 3a
FIG. 3b

DEGRAINING, A THREE STEP PROCESS TO OBTAIN PROPELLANT SAMPLES FROM CASE BONDED MOTORS

BACKGROUND OF THE INVENTION

This invention is related to a method of obtaining propellant samples. More specifically, there is disclosed herein a three step degraining process to obtain propellant samples from a case bonded motor.

Chemical and physical properties of propellants are important in determining the safe and serviceable life of rocket motors. Testing a propellant may show chemical reactions and/or physical changes which occur with age. For example, migration of plasticizers through the propellant, a physical phenomenon, can lead to hardening of the certain areas and localize stresses, resulting in a greater susceptability of these motors to cracking. The cracks, once initiated, may propagate and expose a larger surface to burning. This results in elevated pressures during motor operation, which ultimately lead to motor malfunction. Plasticizers may also modify the burning rates of propellants; migration of this type of plasticizer will change the burning rate profile of the propellant, resulting in different pressure-time and thrusttime curves with age, which is undesirable. An example of this phenomenon is the migration of nitroglicerine in double-based propellant.

Propellant sampling from cartridge-loaded motors is a simple task. The nozzle and igniter are removed and the propellant grain is pushed or pulled from the motor chamber. The propellant grain can be cut and samples can be obtained as desired for testing. However, case-bonded motors present a problem. The propellant is bonded directly to the motor chamber by a liner and previous attempts to obtain propellant samples have been considered extremely dangerous. A need for testing of propellant from case bonded motors has led now to the development of a three step degraining process. The major features of this process, which distinguishes it from conventional methods or other electrochemical methods for obtaining propellant samples from case bonded motors is that it is safety oriented and comprises the use of electrolytic machining to remove two narrow bands of the case to expose the propellant liner, severing of the sample section from the rocket motor by means of a piano wire cutter, and removal of the propellant sample by means of a spool type piano wire cutter.

SUMMARY OF THE INVENTION

Accordingly there is provided by the present invention a process for obtaining propellant samples from case-bonded motors comprising the use of electrolytic machining to remove two narrow bands of the case to expose the propellant liner, severing of the sample section from the rocket motor by means of a piano wire cutter, and removal of the propellant sample by means of a spool type piano wire cutter. The electrolytic machining is accomplished by a pair of insulated harnesses functioning as the cathode of the electrolytic cell, with the motor case being the anode. Electrolyte is circulated through channels formed in the harnesses. The cutting operation use pneumatic drive means to control the piano wire cutter and the entire process is remotely controlled.

OBJECTS OF THE INVENTION

Therefore it is an object of the present invention to provide a means for obtaining propellant samples from case bonded motors.

Another object of the present invention is to provide a means for removing the metal casing from the propellant so that both metal and propellant will not have to be cut simultaneously.

Yet another object of the present invention is to provide a safe means for obtaining propellant samples from case-bonded motors.

Still another object of the present invention is to provide a remotely controlled process for obtaining propellant samples from a case-bonded motor.

A further object of the present invention is to provide an economical means for obtaining propellant samples from a case-bonded motor.

Other objects, advantages, and novel features of the present invention will become apparent from the following detailed description of the invention when considered in conjunction with the accompanying drawings.

BRIEF DESCRIPTION OF THE DRAWINGS

FIG. 2 is a pictorial representation of a motor chamber with harnesses.

FIG. 3a is a front view of the harness.

FIG. 3b is a cross-sectional view of the harness taking a long line AA.

DESCRIPTION OF THE PREFERRED EMBODIMENTS

Figure 1:
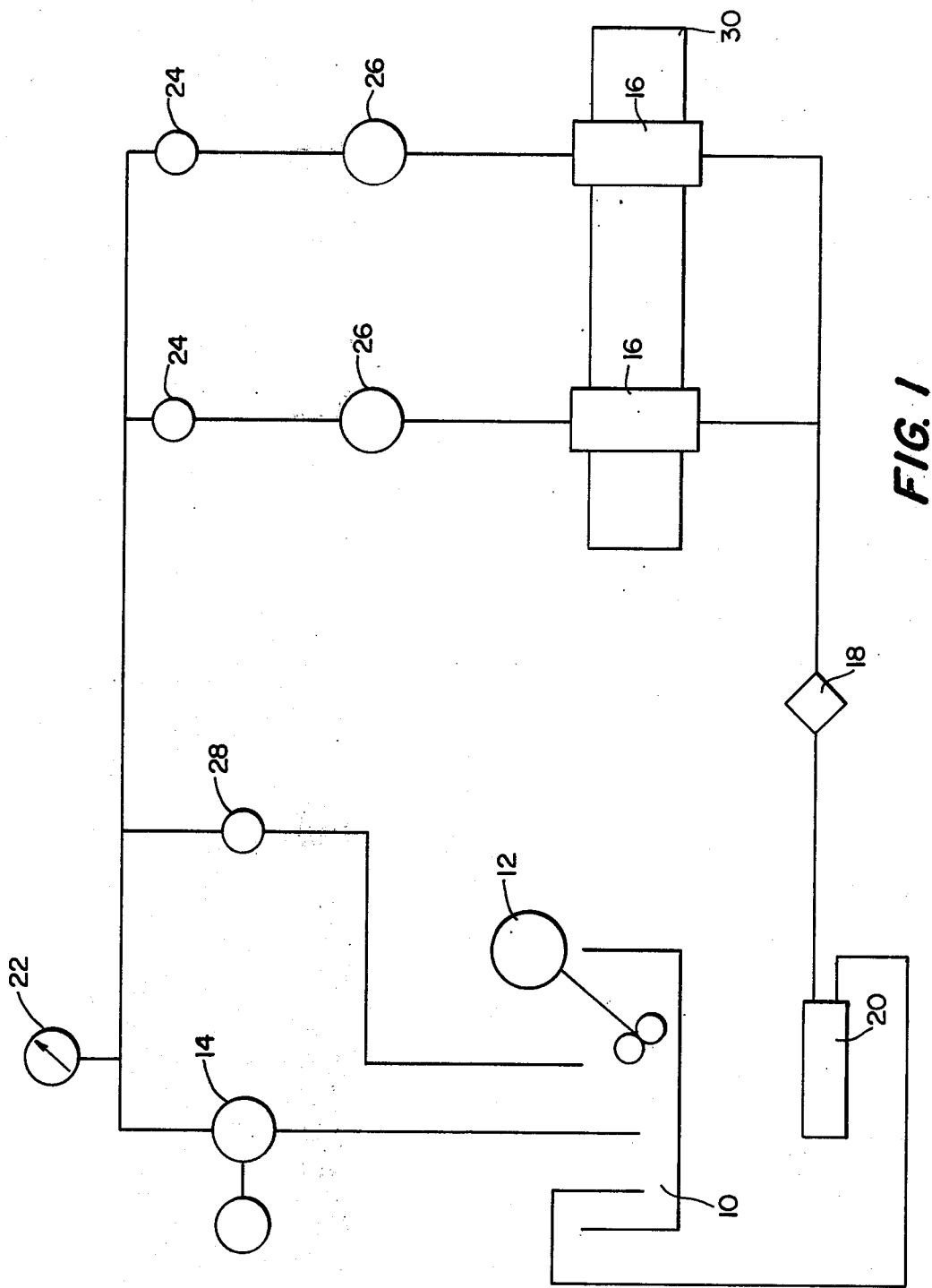
FIG. 1 is a schematic representation of the circulating system.

Referring now to FIG. 1 there shown the electrolytic machining system which basically comprises a reservoir tank 10 with agitator 12, circulating pump 14, cathode harnesses 16, filter 18, and heat exchanger 20. This circulating system can either be mounted in a stationary mode or in a portable mode wherein the units would be connected with quick disconnect couplings.

During the operation of the electrolytic machining process electrolyte flows from the resevoir tank 10 to the circulating pump 14. Pump 14 circulates the electrolyte through the system into the harnesses 16, the filter 18, the heat exchanger 20 and finally back into the reservoir tank 10. The system operates under controlled pressure which is monitored by pressure cell 22. The flow of electrolyte to each cathode harness 16 is regulated by valves 24 and the flow rates are monitored by frequency control meters 26. A bypass valve 28 allows the electrolyte to return directly to the resevoir tank 10. This applies an additional control feature to the flow of electrolyte within the system.

In the preferred mode it should be noted that reservoir tank 10 should be a 60-gallon stainless steel tank with an agitator motor 12 mounted on top. However, it is likewise important to know, that the reservoir tank 10 can be varied in size as well as in the material from which it is made. The only requirement is that care should be taken in selecting material that will not corrode in salt solution.

Although any basic in line filter 18 will serve adequately to remove insoluble material from the electrolyte, the multielement filter tends to be superior. This kind of filter prevents clogging in the line and build up of metallic particles in the harness channels 38, FIG. 3b. Careful filtration will thus allow free and uniform flowing of electrolyte through the entire system during the electrolytic machining process.

Although any basic noncorrodible heat exchanger 20 would work within the present system it has been found that in the preferred mode a shell and tube heat exchanger 20, using a water coolant, will cool the electrolyte and provide superior temperature control during operation. The average operating temperature should be maintained at approximately 95° F. This temperature permits a relatively high speed cutting rate as well as a safe operating temperature for the propellant. It should be noted that the heat exchanger 20 may be eliminated when operating the electrolytic machining process during the winter months of the year because at that time it is not required to lower the temperature of the electrolyte solution.

The entire electrolytic machining operation is remotely controlled. The direct current (dc) power supply unit with builtin safety features supplies the current for the electrochemical process. A strip recorder monitors temperature on the motor chamber, harnesses, and circulating pump meters measure the pressure and rate of flow of electrolyte in the system. Initial cut-through of the chamber is noted when the current drops suddenly. As the metal machining area rapidly decreases, the resistance increases, causing a drop in current. This is monitored by voltage. The upper operating limit for voltage and current in a typical system are 12 volts and 100 amps. At this time the liner, a nonconductor, is exposed to the electrolyte. The machining is then continued until the current levels off at which time the operation is complete and no additional metal need be removed from the chamber 30. The remote control system provides for immediate shut down in cases of emergency or the occurrence of problems. This builtin safety feature is highly desirable from a practical operation standpoint.

One problem confronted during early development of the process was over heating at the harnesses 16 on the motor chamber 30. this, it was analyzed was caused by poor circulation, resulting in built-up of contaminates in the harnesses 16. The problem was resolved by increasing the flow of electrolytes, changing to a pressurized system, and adding the desirable multielement filter.

Referring now to FIG. 2 there are shown the cathode harnesses 16, 16 installed in position on the motor chamber 30. The harnesses 16 can be situated in any circumferential position along the longitudinal length of the motor chamber 30 so that propellant sections can be obtained from any desired area of the motor. Prior to attaching the harnesses 16 to the motor chamber 30 the paint should be removed from the motor chamber so that the steel chamber will be exposed directly to electrolyte.

Referring now to FIGS. 3a and 3b there is shown a typical cathode harness 16. Rubber seals 32 are used to both seal and insulate the harness 16 from the motor chamber 30. During operation a current is impressed on the harness 16, creating an electrolytic cell, with harness 16 as the cathode and the motor chamber 30 as the anode. Thus, the electrolytic machining operation is just the opposite of electroplating, in which the material to be plated is the cathode of an electrolytic cell. Thermocouples 34 are installed on the harnesses 16, on the motor chamber 30 adjacent to the harnesses 16, and at the power leads 36 on the harnesses 16 to monitor temperature. Although any number of harnesses can be operated at a time, the preferred system has been designed to use dual harnesses 16, thus eliminating repetition of the electrolytic machining operation.

Figure 4:
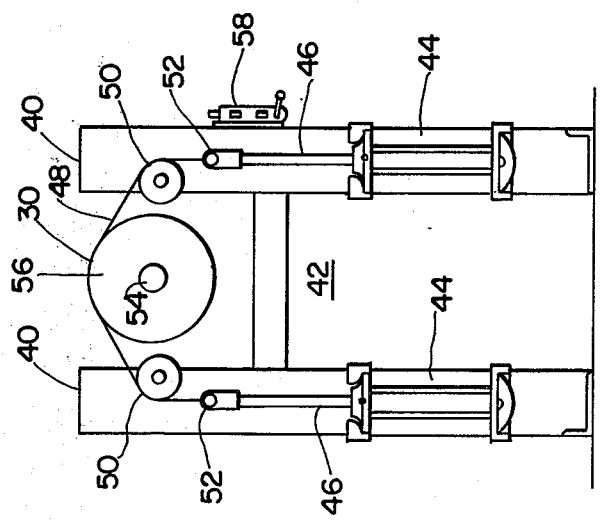
FIG. 4 is a pictorial representation of the piano wire cutter section removal device.

When the electrolytic machining operation has been completed and current has fallen off to a predetermined level, two specified narrow bands of metal casing have been removed. The removal of the metal casing in these two narrow strips exposes the propellant liner which will then be cut by the piano wire cutter section removal system. The propellant which is usually hygroscopic is not exposed at any time either to atmosphere or directly to the electrolyte system. Referring now to FIG. 4 there shown the piano wire cutter section removal system. During operation, the motor 30 is secured in the original machining span or cradle and is placed between the upright 40, 40 of H frame 42 on which dual air filters 44, 44 with pistons 46, 46 are mounted. The piano wire 48 is looped around the motor 30 where the liner has been exposed. The ends of the wire 48 are extended over pullies 50,50 and attached to the clevis 52 of each pinston 44 located on opposite sides of the motor 30. A wooden dowel 54 is inserted into the grain 56 at the propellant center perforation to prevent piano wire 48 from crimping, causing propellant deformation, or breaking. The dowel 54 also supports the grain 56 and helps to produce a clean cut at the point where the wire 48 breaks through the propellant. The cut is made by actuating the four way hand valve 58 located on the H frame 42. The pistons which are in the extended position retract causing the wire 48 to slice through the liner inhibitor and grain 56 and bite into the wooden dowl 54. It should be noted that the preferred system, which is described above, can be modified in numerous ways. First, the piano wire 48 can be replaced by any relatively heavy gauge wire. Furthermore, the pullies 50 can likewise be replaced with any wire guide means, and finally the air cylinders 44 and pistons 46 can be replaced with any similar drive means.

Figure 5:
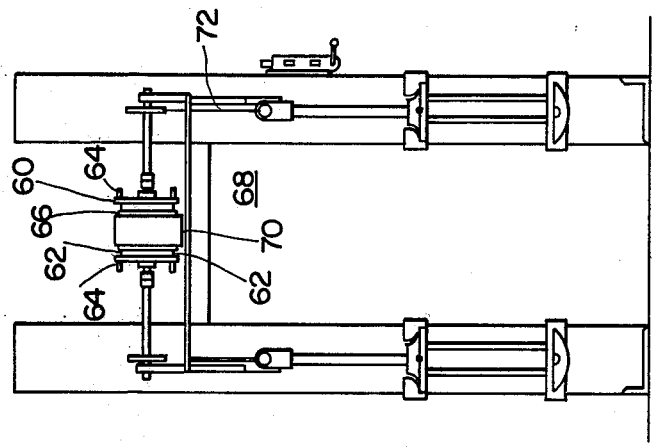
FIG. 5 is a pictorial representation of the piano wire cutter propellant removal system.

Referring now to FIG. 5 there is shown the circular piano wire adapter system for propellant removal. Once the motor section to be sampled has been removed from the overall rocket motor 30, it is then prepared for propellant removal by drilling at least one pair of holes 180° apart longitudinally through the propellant adjacent to the rocket motor case. The section is then placed in the spool type piano wire cutter 60. Piano wires 62, 62 or other similar heavy gauge wire are passed through the two holes in the propellant and secured to the spools on opposite sides of the grain seat. After the wires 62 are torqued, the spools 64 are rotated about 180° degrees separating the propellant 56 from the case 66. The spool cutter assembly 68 is designed to work as a removable attachment to the existing H frame 42 of the piano wire cutting system used for section removal operations. The assembly 68 is mounted on a based plate 70 which is positioned and secured to the H frame 42. With the pistons 46, 46 in the extended position, one end of the cable 72 is attached to each piston 46. The other end is looped over the sheave of the cutter and is secured in such a manner that when the pistons are retracted the cutter spool assembly 60 rotates approximately three quarters of a turn. The piano wires 62 which are secured to the cutter spool 64 after being passed through the holes drilled in the propellent section 56 are thus forced through the propellant 56 in a circular direction and the propellant 56 is separated from the case 66.

What is claimed and is desired to be secured by Letters Patent of the United States is:

1. A degraining process for obtaining propellant samples from metal case-bonded rocket motors, comprising the steps of:
   (1) electrolytically machining two circumferential slots through the metal case to expose the propellant liner;
   (2) using a piano wire cutter to cut through the two exposed strips of the propellant liner and the adjacent propellant thereby separating a metal case-bonded section from the balance of the metal case-bonded rocket motor; and
   (3) using a rotational piano wire cutter to cut and separate the propellant from the metal case.

2. The process of claim 1 wherein step (1) is continued until the current through the electrolyte stops decreasing, indicating that the metal case has been cut through.

3. The process of claim 2 wherein step (1) is performed by remote control.

* * * * *